(12) United States Patent
Huang et al.

(10) Patent No.: US 9,456,995 B2
(45) Date of Patent: Oct. 4, 2016

(54) METHODS FOR INHIBITION OF BNIP3 AND PREVENTION AND TREATMENT OF ISCHEMIA REPERFUSION INJURY BY TETRA-O-METHYL NORDIHYDROGUAIARETIC ACID

(71) Applicant: THE JOHNS HOPKINS UNIVERSITY, Baltimore, MD (US)

(72) Inventors: Ru Chih Huang, Baltimore, MD (US); Kotohiko Kimura, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/415,163

(22) PCT Filed: Jul. 18, 2013

(86) PCT No.: PCT/US2013/051074
§ 371 (c)(1),
(2) Date: Jan. 16, 2015

(87) PCT Pub. No.: WO2014/015136
PCT Pub. Date: Jan. 23, 2014

(65) Prior Publication Data
US 2015/0209304 A1    Jul. 30, 2015

Related U.S. Application Data

(60) Provisional application No. 61/672,884, filed on Jul. 18, 2012.

(51) Int. Cl.
*A61K 31/085*    (2006.01)
*A61K 31/09*    (2006.01)

(52) U.S. Cl.
CPC ............ *A61K 31/09* (2013.01); *A61K 31/085* (2013.01)

(58) Field of Classification Search
USPC ........................................ 514/715, 718, 721
See application file for complete search history.

(56) References Cited

U.S. PATENT DOCUMENTS 3,906,004 A    9/1975    Perry

FOREIGN PATENT DOCUMENTS

WO    2001-28494 A2    4/2001
WO    2011-026060 A2    3/2011

OTHER PUBLICATIONS

Lu; Medical Science Monitor, Apr. 28, 2010 16(5), RA93-R100, p. 1-15.*
Lu, JM., et al., "Molecular mechanisms and clinical applications of nordihydroguaiaretic acid (NDGA) and its derivatives: an update", Med Sci Monit, Apr. 28, 2010, vol. 16, No. 5, RA93-R100.

* cited by examiner

*Primary Examiner* — Pancham Bakshi
(74) *Attorney, Agent, or Firm* — John Hopkins Technology Transfer

(57) ABSTRACT

Provided herein are methods for prevention and treatment of ischemia-reperfusion (IR) injury in the cardiac myocytes of a subject, by administration to the subject, a compound of formula I, or a salt, solvate, or stereoisomer thereof, in a sufficient amount either prior to, or during and/or after an ischemic event to mitigate or prevent IR injury to the cardiac tissue. Pharmaceutical compositions including the compound of formula I, or a salt, solvate, or stereoisomer thereof, and/or at least one additional therapeutic agent, are also provided.

4 Claims, 4 Drawing Sheets

METHODS FOR INHIBITION OF BNIP3 AND PREVENTION AND TREATMENT OF ISCHEMIA REPERFUSION INJURY BY TETRA-O-METHYL NORDIHYDROGUAIARETIC ACID

CROSS-REFERENCE TO RELATED APPLICATIONS

This application is a 35 U.S.C. § 371 U.S. national entry of International Application PCT/US2013/051074, having an international filing date of Jul. 18, 2013, which claims the benefit of U.S. Provisional Application No. 61/672,884, filed Jul. 18, 2012, the content of each of the aforementioned applications is herein incorporated by reference in their entirety.

BACKGROUND OF THE INVENTION

Myocyte cell loss is a prominent and important pathogenic feature of cardiac ischemia (myocardium infarction). It is widely known that a great amount of cardiac cell loss after infarction happens by a mechanism called ischemia/reperfusion (IR) injury. The IR injury allows for massive cell death to happen only after the blood supply (thus oxygen supply) is reestablished after cardiac ischemia (thus hypoxia) triggers cell death. This indicates that normoxic condition after hypoxia is a key for massive cardiac cell loss after myocardium infarction. Limiting this loss is a desirable therapeutic goal, but the development of truly effective strategies to achieve that goal requires an understanding of the mechanisms by which ischemia triggers cell death. Investigators have turned to isolated and cultured cardiomyocytes to identify signaling pathways involved in the response to ischemia and to systematically test the effectiveness of pro survival signaling pathways and various anti-death molecules against ischemia-associated cellular insults, such as hypoxia.

Reperfusion is the most effective strategy to save the ischemic tissue, but it can cause additional damage, leading to cell dysfunction and death. The pathology of ischemia-reperfusion (IR) injury has been observed in the heart, brain, liver, and kidney.

BNIP3 stands for Bcl-2 and nineteen-kilodalton interacting protein-3, and is a member of the Bcl-2 protein family. Bcl-2 proteins have been implicated in the control of both apoptotic and necrotic cell death and in guarding mitochondrial integrity. They share up to 4 conserved regions of homology known as Bcl-2 homology domains (BH1, BH2, BH3, and BH4), which mediate interactions among the various family members, and are divided functionally into antiapoptotic and proapoptotic members. Many of these proteins normally reside in membranous cellular structures, including mitochondria, endoplasmic reticulum, and the nuclear envelope or are recruited to such structures (principally the mitochondria) during the execution of cell death signaling pathways. Antiapoptotic members, such as Bcl-2, Bcl-XL, Mcl-I, AI, Bcl-W, display sequence homology throughout all 4 BH domains. Proapoptotic members that antagonize the activity of many pro survival proteins and induce cell death when overexpressed, display homology to fewer BH domains. Some, like Bax and Bak, contain BH1, BH2, and BH3 domains, whereas many others (Bad, Bid, Bik, Bim, BimL, Blk, and Noxa) possess only the BH3 domain (BH3-only proteins).

BNIP3 is the founding member of small group of BH3-only proteins that includes BNIP3, NixIBNIP3L, and BNIP3H. In contrast to Bid and Bad, the proapoptotic activity of BNIP3 and Nix is regulated through transcriptional mechanisms that involve the HIF complex. Thus, the promoter for BNIP3 contains a functional binding site for the HIF transcriptional complex (hypoxia response element, HRE) and its mRNA and protein expression are dramatically increased in multiple cell types in response to reduced oxygen concentration. In cultured cells, increased expression of BNIP3 appears to be part of a second wave of hypoxia induced protein accumulation, occurring late relative to other well-characterized HIF-inducible genes that are involved in promoting angiogenesis, glycolytic metabolism, and survival (e.g. erythropoietin, VEGF, heme oxygenase, hexokinase, and IGF2).

It has been shown that (i) BNIP3 expression is dramatically increased in response to hypoxia, (ii) enforced expression of BNIP3 causes cell death in normoxic cardiomyocytes, and (iii) enforced expression of a BNIP3 mutant lacking its transmembrane domain (BNIP3L1TM) partially blocks hypoxia-induced cell death.

Therefore, there still exists a need for novel methods and drugs to mitigate or prevent IR induced cell death in cardiac myocytes as a result of cardiac arrest, infarct, or due to surgical intervention.

SUMMARY OF THE INVENTION

The inventors have found that suppression of BNIP3 expression by administration of an inhibitor of BNIP3 expression is beneficial for improving heart conditions after infarction. The present invention shows that the compound of formula I, known as tetra-o-methyl nordihydroguaiaretic acid (M4N), or its salts, solvates, or stereoisomers thereof, is useful for the prevention or treatment of IR injury in subjects having cardiac failure or suffering from an ischemic event.

In accordance with an embodiment, the present invention provides a compound of formula (I):

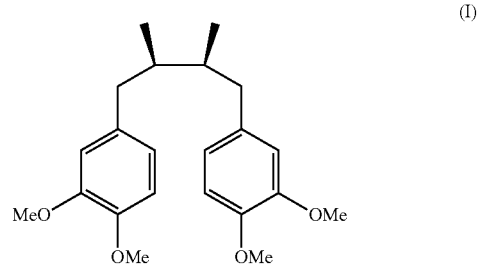 [SMILES: COc1ccc(C[C@@H](C)[C@@H](C)Cc2ccc(OC)c(OC)c2)cc1OC]

(I)

or a solvate, or stereoisomer thereof, for use in the prevention or treatment of ischemia-reperfusion injury (IR) in the cardiac myocytes of a subject comprising administering the compound of formula (I), or a solvate, or stereoisomer thereof, in a sufficient amount to inhibit IR injury in the cardiac myocytes of a subject.

In accordance with another embodiment, the present invention provides compound of formula (I):

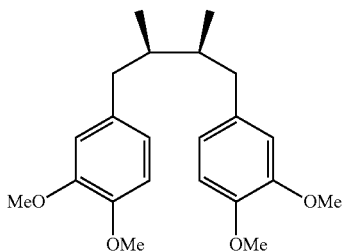

or a solvate, or stereoisomer thereof, for use in the inhibition of expression of BNIP3 in the cardiac myocytes of a subject comprising administering the compound of formula (I), or a solvate, or stereoisomer thereof, in a sufficient amount to inhibit expression of BNIP3 protein in the cardiac myocytes of a subject.

In an embodiment, the present invention provides a pharmaceutical composition comprising a compound, solvate, or stereoisomer of any of the above described compounds, and a pharmaceutically acceptable carrier.

In another embodiment, the present invention provides pharmaceutical composition comprising a compound, solvate, or stereoisomer of any of the above described compounds, at least one additional therapeutic agent, and a pharmaceutically acceptable carrier.

In accordance with a further embodiment, the present invention provides a method for the prevention of IR injury in the cardiac myocytes of a subject comprising administering to the subject prior to the ischemic event, the compound of formula (I), or a solvate, or stereoisomer thereof, or a pharmaceutical composition comprising the compound of formula (I), or a solvate, or stereoisomer thereof, in a sufficient amount to decrease the amount of IR injury.

In accordance with still another embodiment, the present invention provides a method for the treatment of IR injury in the cardiac myocytes of a subject comprising administering to the subject during and/or after to the ischemic event, the compound of formula (I), or a solvate, or stereoisomer thereof, or a pharmaceutical composition comprising the compound of formula (I), or a solvate, or stereoisomer thereof, in a sufficient amount to decrease the amount of IR injury.

In accordance with an embodiment, the present invention provides a method for prevention or inhibition of IR injury in the cardiac myocytes of a subject about to undergo a surgical procedure capable of causing IR injury comprising administering the compound of formula (I), or a solvate, or stereoisomer thereof, or a pharmaceutical composition comprising the compound of formula (I), or a solvate, or stereoisomer thereof, to the subject prior to the procedure, in an amount effective to prevent or reduce IR injury.

DETAILED DESCRIPTION OF THE INVENTION

Figure 1:
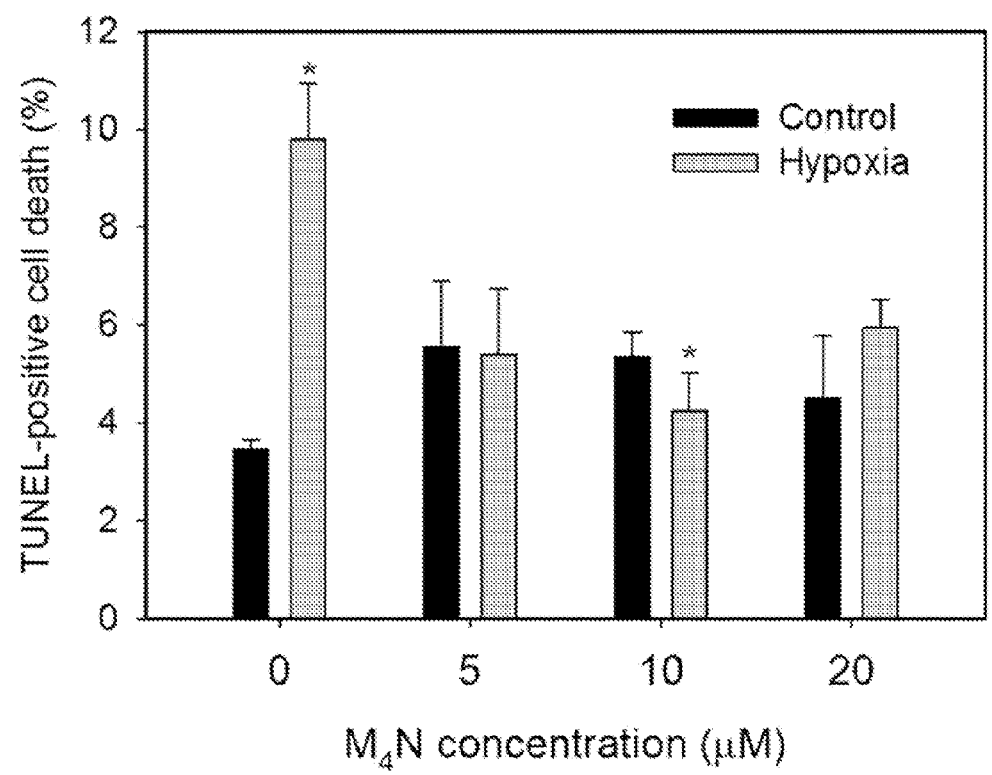
FIG. 1 shows Effect of M4N on TUNEL positive cell death induced by hypoxia in HL-1 mouse heart cells. The cells were treated with various concentrations of M4N and incubated under hypoxia for 6 hours followed with under normoxia for 18 hours. The cell death was measured with TUNEL assay. The asterisks (*) indicate statistical significant difference between them by t-test at the error rate less than 1%.

IR injury is a major cause of massive myocyte loss after cardiac infarction. BNIP3 is considered to be a major contributor for aggravating the IR injury after infarction, and the rationale for utilizing BNIP3 as a target for treatment of cardiac failure is well established. Thus, the present inventors hypothesized that the blockage of BNIP3 by any means will prevent massive cardiac cell loss after infarction as long as the treatment does not have adverse side effects on patients.

In accordance with some embodiments, the present inventors now show M4N to be a very effective inhibitor for BNIP3 expression. In fact, M4N at concentrations of 5-20 μM, reduced cell death of HL-1 mouse heart cells induced by hypoxic treatment. The present invention also shows that the majority of cell death induced by hypoxia in HL-1 cells is necrotic, because the TUNEL assay only detected the cell death accompanied with DNA fragmentation which is a hallmark of apoptosis. M4N reduced cell death whether measured by Trypan blue exclusion assay or TUNEL assay, indicating that the drug was effective to suppress both necrosis and apoptosis for hypoxia-mediated cell death. Moreover, M4N at the concentration of about 20 μM was able to reduce cell death induced by UCN-01 in HL-1 cells to some extent, indicating that the protective activity of M4N for the cells is not confined to hypoxia-related cell death insult.

In accordance with an embodiment, the present invention provides a compound of formula (I):

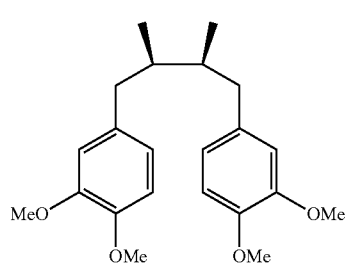

or a solvate, or stereoisomer thereof, for use in the prevention or treatment of ischemia-reperfusion injury (IR) in the cardiac myocytes of a subject comprising administering the compound of formula (I), or a solvate, or stereoisomer thereof, in a sufficient amount to inhibit IR injury in the cardiac myocytes of a subject.

In an embodiment, the present invention provides a pharmaceutical composition comprising a compound, solvate, or stereoisomer of any of the above described compounds, and a pharmaceutically acceptable carrier.

In another embodiment, the present invention provides pharmaceutical composition comprising a compound, solvate, or stereoisomer of any of the above described compounds, at least one additional therapeutic agent, and a pharmaceutically acceptable carrier.

Included within the compounds of the present invention are the tautomeric forms of the disclosed compounds, isomeric forms including diastereoisomers, and the pharmaceutically-acceptable salts thereof.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

With respect to the pharmaceutical compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include solid compositions such as solid-state carriers or latex beads.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

The choice of carrier will be determined, in part, by the particular pharmaceutical composition, as well as by the particular method used to administer the composition. Accordingly, there are a variety of suitable formulations of the pharmaceutical composition of the invention.

As used herein, the term "IR injury" means microvascular dysfunction that is manifested as impaired endothelium-dependent dilation in arterioles, enhanced fluid filtration and leukocyte plugging in capillaries, and the trafficking of leukocytes and plasma protein extravasation in postcapillary venules. Activated endothelial cells in all segments of the microcirculation produce more oxygen radicals, but less nitric oxide, in the initial period following reperfusion. The resulting imbalance between superoxide and nitric oxide in endothelial cells leads to the production and release of inflammatory mediators (e.g. platelet-activating factor, tumor necrosis factor) and enhances the biosynthesis of adhesion molecules that mediate leukocyte-endothelial cell adhesion. Some of the known risk factors for cardiovascular disease (hypercholesterolemia, hypertension, and diabetes) appear to exaggerate many of the microvascular alterations elicited by ischemia and reperfusion. The inflammatory mediators released as a consequence of reperfusion also appear to activate endothelial cells in remote organs that are not exposed to the initial ischemic insult. This distant response to IR injury can result in leukocyte-dependent microvascular injury that is characteristic of the multiple organ dysfunction syndrome. Often in cardiac tissue, the resulting IR injury is the cause of subsequent heart failure. Reperfusion injury may be responsible for up to 50% or more of the ultimate infarct size and is an important contributor to post-surgical mortality and morbidity as well. Clinically, the extent of myocardial salvage by early reperfusion may not be realized because of cell injury and death initiated by reperfusion itself.

In accordance with another embodiment, the present invention provides compound of formula (I):

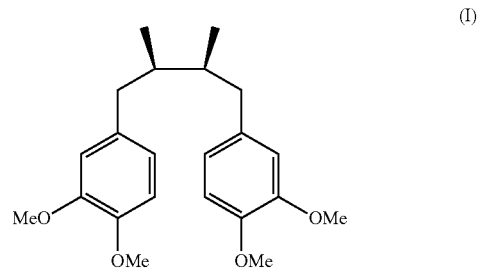 [SMILES: COc1ccc(C[C@@H](C)[C@@H](C)Cc2ccc(OC)c(OC)c2)cc1OC]

or a solvate, or stereoisomer thereof, for use in the inhibition of expression of BNIP3 in the cardiac myocytes of a subject comprising administering the compound of formula (I), or a solvate, or stereoisomer thereof, in a sufficient amount to inhibit expression of BNIP3 protein in the cardiac myocytes of a subject.

As used herein, the term "inhibit expression" means that the amount of BNIP3 protein expressed by the cardiac myocytes treated with the compound of formula (I), or a salt, solvate, or stereoisomer thereof, is measurably less than the amount of BNIP3 protein expressed by either control or untreated cardiac myocytes.

It will be understood to those of skill in the art that the term "therapeutic agent" is any agent capable of affecting the structure or function of the body of a subject or is an agent useful for the treatment or modulation of a disease or condition in a subject suffering therefrom. Examples of therapeutic agents can include any drugs known in the art for treatment of disease indications.

In accordance with a further embodiment, the present invention provides a method for the prevention of IR injury in the cardiac myocytes of a subject comprising administering to the subject prior to the ischemic event, the compound of formula (I), or a solvate, or stereoisomer thereof, or a pharmaceutical composition comprising the compound of formula (I), or a solvate, or stereoisomer thereof, and a sufficient amount to decrease the amount of IR injury.

In accordance with still another embodiment, the present invention provides a method for the treatment of IR injury in the cardiac myocytes of a subject comprising administering to the subject during and/or after to the ischemic event, the compound of formula (I), or a solvate, or stereoisomer thereof, or a pharmaceutical composition comprising the compound of formula (I), or a solvate, or stereoisomer thereof, in a sufficient amount to decrease the amount of IR injury.

In accordance with an embodiment, the additional therapeutic agent is an agent that can mitigate or prevent IR injury, or another cardiac therapeutic agent. Examples of agents which mitigate or prevent IR injury include, for example, allopurinol, adenosine, oxygen free radical scavengers, antioxidants, inhibitors of neutrophils, nitric oxide, adenosine-related agents, inhibitors of the renin-angiotensin system, endothelin receptor antagonists, $Na^+/H^+$ exchange inhibitors, and anti-apoptotic agents, such as IL-10.

Examples of other cardiac therapeutic agents include, for example, calcium channel blockers, beta-blockers, digoxin and other cardiac glycosides, salicylic acid, vasodilators, ACE inhibitors, diuretics, inotropic agents, antiplatelet agents, anticoagulants, nitrates, thrombolytic agents, and antiarrhythmic agents.

In accordance with an embodiment, the present invention provides a compound, salt, solvate, or stereoisomer of any of the above described compounds, for use in preparing a medicament, preferably a medicament for use in the prevention or treatment of IR injury in the cardiac myocytes of a subject.

For purposes of the invention, the amount or dose of the compositions of the present invention that is administered should be sufficient to effectively target the cell, or population of cells in vivo, such that IR injury or death in the target cell or population of cells is prevented or mitigated in the subject over a reasonable time frame. The dose will be determined by the efficacy of the particular pharmaceutical formulation and the location of the target population of cells in the subject, as well as the body weight of the subject to be treated.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se, as well as pharmaceutically acceptable, pharmacologically active salts, esters, amides, prodrugs, metabolites, analogs etc.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated. By way of example, and not intending to limit the invention, the dose of the pharmaceutical compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight.

In another embodiment, the dose of the pharmaceutical compositions of the present invention can be at a concentration from about 100 µM to about 50 µM, preferably from about 1 µM to about 20 µM.

The terms "treat," and "prevent" as well as words stemming there from, as used herein, do not necessarily imply 100% or complete treatment or prevention of IR injury. Rather, there are varying degrees of treatment or prevention of which one of ordinary skill in the art recognizes as having a potential benefit or therapeutic effect. In this respect, the inventive methods can provide any amount of any level of treatment or prevention of IR injury or cardiac myocyte cell death in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated.

As used herein, the terms "effective amount" or "sufficient amount" are equivalent phrases which refer to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease, such IR injury.

In accordance with an embodiment, the present invention provides a method for prevention or inhibition of IR injury in the cardiac myocytes of a subject about to undergo a surgical procedure capable of causing IR injury comprising administering the compound of formula (I), or a solvate, or stereoisomer thereof, or a pharmaceutical composition comprising the compound of formula (I), or a solvate, or stereoisomer thereof, to the subject prior to the procedure, in an amount effective to prevent or reduce IR injury.

It will be understood by those of skill in the art, that the administration of the compound of formula (I), or a solvate, or stereoisomer thereof, or a pharmaceutical composition comprising the compound of formula (I), or a solvate, or stereoisomer thereof can be performed in situations where a subject is to have cardiac surgery. In such situations, the heart is subject to temporary arrest and/or ischemia during the actual surgical procedure on the heart. Administration of the compounds and compositions of the present invention at least 30 minutes to 6 hours before the procedure will reduce or prevent subsequent IR damage to the cardiac tissues.

EXAMPLES

Cell Culture. HL-1 mouse heart cell line was a kind gift from Dr. Claycomb (LSU Health Science Centers, New Orleans La.) (Proc. Natl. Acad. Sci. U.S.A., 95: 2979-84 (1998)). HL-1 cells were cultured in Claycomb medium (Sigma, Saint Louis, Mo.) supplemented with FBS (10%), Norepinephrine (0.1 mM), L-Glutamine (2 mM), penicillin (100 units/ml) and streptomycin (100 µg/ml). Drugs were dissolved in dimethyl sulfoxide at the final concentrations in the medium less than 0.1%. When the cells were indicated to be cultured under hypoxic conditions, the cells were incubated at the oxygen concentration of 0.5% in the hypoxic chamber (BioSpherix Ltd, Lacona, N.Y.).

Reagents. Terameprocol (M4N) (10 mg/ml in CPE 25/30 formulation) was supplied by Erimos Pharmaceutical, L.L.C. (Raleigh, N.C.), according to the method described (Anti-Cancer Drugs 18:933-939 (2007)). Etoposide, rapamycin, UCN-01, and Baflomycin $A_1$ were all from Sigma. Anti-BNIP3 mouse monoclonal antibody was from Abcam (Cambridge, Mass.). Anti-Actin monoclonal antibody was from Sigma.

Cell death assay. Terminal deoxynucleotidyl transferase dUTP nick end labeling (TUNEL) assay was conducted by using TUNEL apoptosis detection kits (Upstate, Temecula, Calif.), with some modifications. The cells were cultured in 12-well microwell culture dishes (Corning Inc., Corning, N.Y.). After the treatment, both the cells floating in the tissue culture medium and those attached to the bottoms of wells were collected together into plastic tubes. After the cells were spun down at 700 rpm, they were fixed with 10% formaldehyde in PBS-(−) (phosphate buffered saline without calcium and magnesium) for 5 min and stored in PBS-(−). The fixed cell samples were put on glass slides and dried in the air. The slides were first incubated in the solution containing 0.05% Tween-20, 0.2% BSA in PBS-(−) for 15 minutes at room temperature. The samples were then treated with terminal deoxytransferase and biotin-dUTP included in the TUNEL assay kit for 60 minutes at room temperature, according to the manufacturer's protocol. After the incubation, the samples were incubated with avidin-biotin complex (ABC reagent, Vector Laboratory Inc., Burlingame, Calif.) for 30 minutes at room temperature. After the extensive washing with PBS-(−), the DNA terminal ends of the samples were exposed by the peroxidase reaction using DAB as a substrate (peroxidase substrate kit, Vector Laboratory Inc.). The samples were counterstained by methyl green and embedded in VectaMount (Vector Laboratory Inc.).

For the Trypan blue exclusion assay, the cells were washed with PBS (−) once and resuspended in PBS (−) again. One part of the resuspended cell solution was mixed with one part of 0.4% Trypan blue solution (Sigma). In about 5 to 15 minutes the numbers of both the cells without staining and the cells with staining were counted. The percentages of the number of the cells with staining to the total cell number (which equals to the number of the cells with staining and that of the cells without staining) were calculated.

Western blotting. After cells had been grown in 25 mm² flasks and treated with reagents, the cells were washed with PBS (−) three times and suspended in RIPA buffer (150 mM NaCl, 50 mM Tris-HCl (pH 8.0), 0.1% SDS, 1% NP40, and 0.5% deoxycholate) supplemented with protease inhibitor cocktail (Calbiochem, San Diego, Calif.). The sample volumes were adjusted by the total protein amount. Protein assay was performed by Bio-Rad Protein Assay (Bio-Rad Laboratories, Inc. Hercules, Calif.). The samples were resolved by the standard SDS-polyacrylamide gel electrophoresis and transferred to nitrocellulose membrane (Amersham Biosciences, Bjorkgatan, Sweden). The membranes were blocked with skim milk, and incubated with primary antibodies at 4° C. overnight and then with secondary antibody conjugated with horse radish peroxidase at room temperature for 2 hours. The signals were detected by western blot chemiluminescence reagent plus (New England Nuclear Life Science Products, Boston, Mass.).

Measurement of mitochondrial permeability transition pore (mPTP) openings. The mPTP was measured by Image-iT LIVE Mitochondria Transition Pore Assay Kit (Molecular Probes, Eugene Oreg.). The cells were first washed with Hank's Balanced Salt Solution (HBSS) with sodium bicarbonate, calcium, and magnesium that also included HEPES (10 mM), L-glutamine (2 mM) and succinate (100 µM) to support healthy mitochondrial function (modified HBSS). The cells were then labeled with calcein-AM (1.0 µM) and MitoTracker Red CMSRos dye (200 µM) in modified HBSS with 1 µM $CoCl_2$ for 15 minutes. After the medium was changed to the normal HL-1 culture medium, the cells were treated with M4N at various concentrations (0, 5, 10, 20, 40, and 80 µM). The cells were incubated under hypoxia for 6 hours, followed with under normoxia for 8 hours. After the cells were washed with modified HBSS, they were examined by B29/Zeiss LSM 510 META laser confocal microscope (Carl Zeiss, Jena, Germany) for calcein at FITC settings and for MitoTracker at rhodamine settings.

Example 1

Effect of M4N on the cell death induced by hypoxia in mouse heart HL-1 cells. Previously it was found that M4N reduced the expression of BNIP3 in various cancer cells such as human prostate cancer LNCaP and PC3 cells, human breast cancer MCF-7 cells, or human hepatic cancer HepG2 cells, which indicated that the inhibitory effect of M4N on BNIP3 expression is ubiquitous. Since it is technically difficult to investigate the direct drug effect to the live heart, HL-1 mouse heart tissue culture was used as a model system. HL-1 cells are considered to be extremely close to normal heart cells by genetic analysis and physiological characteristics. For this reason, HL-1 cells are well suited for this investigation. For the hypoxia treatment the cells were cultured under 0.5% oxygen concentration in a hypoxic chamber for 6 hours and returned the cells back to normoxic condition in a normal culture chamber, and then cell death was measured 18 hours later. This procedure was used to mimic the condition representing myocardial ischemia/reperfusion injury which has been considered to be a major cause of cardiac failure after myocardial infarction.

Figure 2:
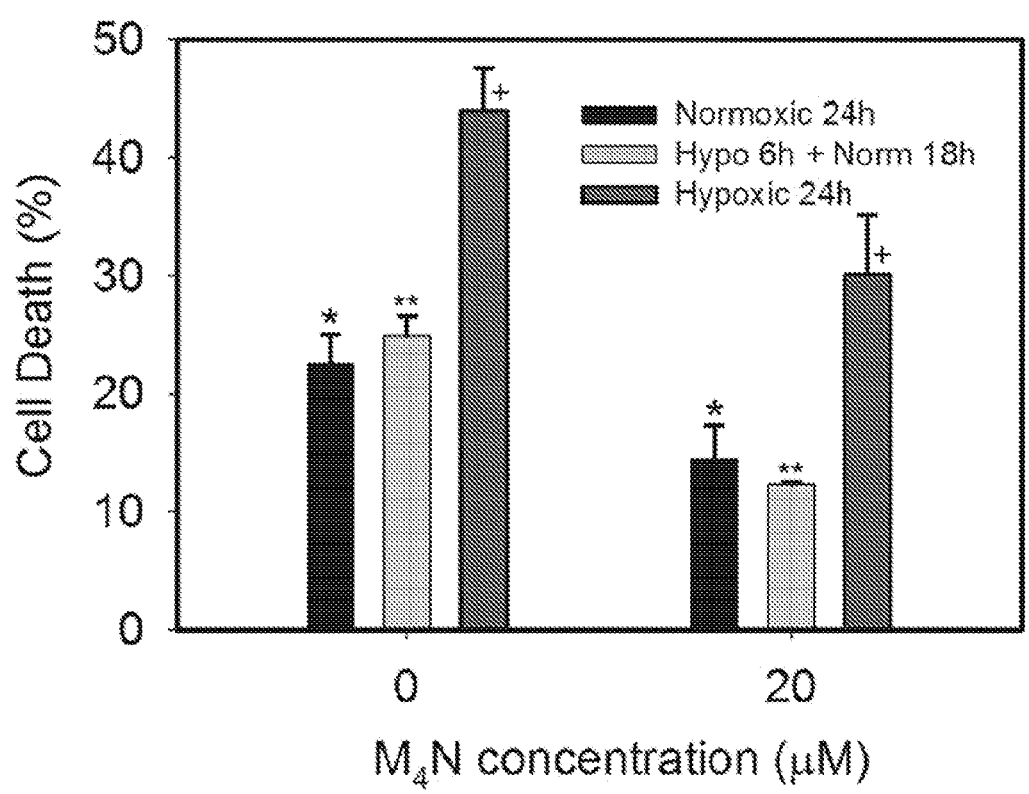
FIG. 2 depicts the effect of M4N on the cell death induced by hypoxia in mouse heart HL-1 cells. The effect of M4N at 20 μM and 40 μM on hypoxia-induced cell death in HL-1 cells was examined by Trypan Blue exclusion assay. Data are presented as means (+/−) SD in triplicates. The differences between two groups designated by the symbols (*, **, +) were statistically significant by t-test at the error rate of less than 2% (*), 0.1% (**), and 1% (+) respectively.

First, TUNEL-positive cell death induced by 6 hour hypoxia treatment followed with 18 hour normoxia treatment in HL-1 cells (FIG. 1) was examined. The data showed that M4N at 5-20 µM reduced the cell death induced by hypoxia. However, the level of the cell death detected by TUNEL assay was rather small. Next, cell death was quantified by Trypan blue exclusion assay (FIG. 2). The data showed significantly greater numbers of cell death by Trypan blue exclusion assay than by TUNEL assay (FIG. 1), which indicated that the majority of cell death in HL-1 cells by hypoxia occurred through necrosis rather than apoptosis since TUNEL assay only picks up the cell death accompanied with significant amount of DNA cleavage which is characteristics of apoptosis. The Trypan blue exclusion assay showed that M4N at 20 µM reduced the cell death induced by hypoxia (either 6 hour hypoxia with additional 18 hour normoxia treatment or 24 hour hypoxia treatment). Additionally M4N at 20 µM reduced cell death compared with the control even under normoxic condition as well. The data also showed that a certain amount of cells (about 20% positive cells of the total measured by Trypan blue exclusion assay) were already considered to be dead even in the control culture. This is one of the indications that HL-1 cells are similar in physiology to normal human myocytes, which are known to be difficult to maintain under tissue culture conditions. The data overall showed that M4N suppressed TUNEL-positive cell death at concentrations around 5-20 µM, as well as the cell death detectable by Trypan blue exclusion assay, which indicated that M4N in this concentration range suppressed both necrosis and apoptosis in HL-1 cells treated by hypoxia.

Example 2

Figure 3:
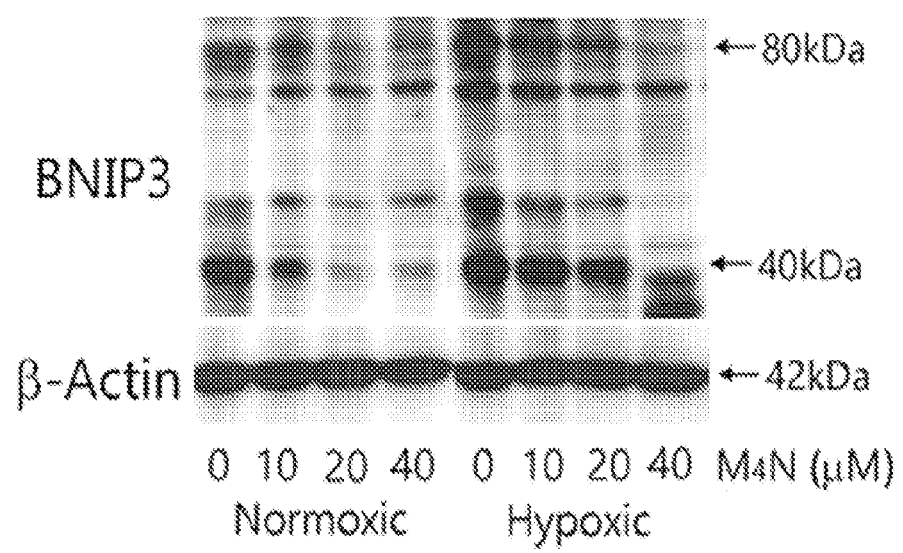
FIG. 3 shows the effect of M4N on the expression of BNIP3 in HL-1 mouse heart cells under hypoxia. HL-1 cells were incubated under hypoxia for 6 hours followed with normoxia for 18 hours. As a control, HL-1 cells were incubated under normoxia for 24 hours. Protein expression was measured by western blotting. β-Actin was used as a control.

Effect of $M_4N$ on BNIP3 expression in mouse heart HL-1 cells. FIG. 3 shows that BNIP3 expression was indeed suppressed by M4N treatment at the concentrations of 10-40 µM in HL-1 cells incubated under hypoxia for 6 hours and then under normoxia for 18 hours. These are the same conditions used for the cell death assay shown in FIGS. 1 and 2. Interestingly it was shown that BNIP3 gene promoter contained numerous GC boxes capable of binding with SP1, which suggested that M4N was likely suppressed BNIP3 expression through its competitive inhibitory effect on the binding of SP1 to these GC boxes.

Example 3

Effect of M4N on mitochondria permeability transition pore (mPTP) openings. BNIP3 was reported to mediate mitochondrial dysfunction via opening of the mPTP and via activation of Bax/Bak. The mPTP is thought to mainly play a role in necrosis, whereas the Bax/Bak channel is involved in apoptotic cell death. Since present invention (FIGS. 1 and 2) indicates that necrosis was a predominant way of cell death in the experimental system, the effect of M4N on mPTP openings was examined. Confocal microscopy indicated that M4N suppressed mPTP openings induced by hypoxia at the concentrations of 5-20 µM (data not shown), which is comparable with the cell death data showing that M4N suppressed hypoxia-mediated cell death at 5-20 µM (FIG. 2). The data also indicated that the mechanism of cell death suppression by M4N in HL-1 cells treated with IR insult was through inhibition of hypoxia-inducing BNIP3 upregulation and then blockage of mPTP openings.

Example 4

Figure 4:
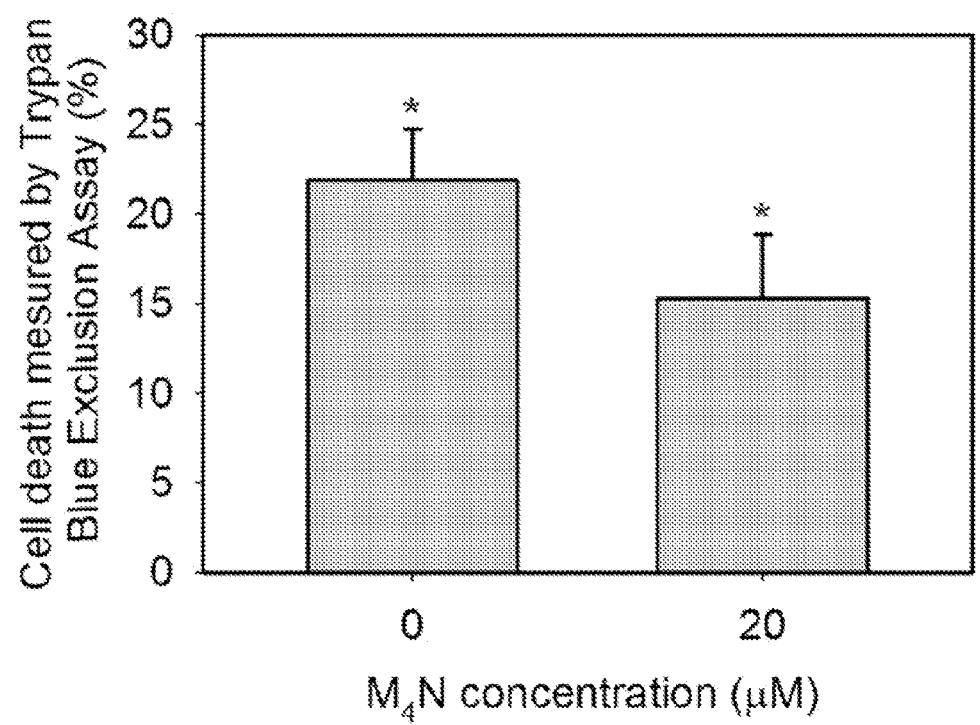
FIG. 4 depicts the effect of M4N on cell death induced by UCN-01 treatment in HL-1 mouse heart cells. The cells were treated with M4N followed with UCN-01 (0.2 μM) treatment for 24 hours. The cell death was measured with Trypan Blue exclusion assay. The asterisk indicates a statistically significant difference by t-test at the error rate of less than 2%.

Effect of $M_4N$ on UCN-01-inducing cell death. Next, the effect of $M_4N$ on the cell death induced by UCN-01, an anticancer drug, in HL-1 cells (FIG. 4) was examined. The present data indicate that $M_4N$ reduced UCN-01-mediated cell death at concentrations around 20 µM in HL-1 cells, as measured with Trypan blue exclusion assay. The data show that the protective effect of $M_4N$ against cell death-inducing insults is not limited to hypoxia-inducing cell death.

The mechanism of suppression of BNIP3 expression by M4N is not known. The inventors' own internal data indicate that M4N blocks BNIP3 expression in LNCaP human prostate cancer cells at the transcription level (data not shown). Since there are numerous GC boxes capable of binding with SP1 in the BNIP3 promoter, M4N could be suppressing BNIP3 expression by competitive binding to these GC boxes. BNIP3 induces mitochondrial cell death stimuli by activating Bax/Bad and permeabilizing mitochondrial membrane. The present invention shows that M4N indeed suppresses the openings of mPTP induced by hypoxia in HL-1 cells, which supports the mechanistic model that M4N protected HL-1 cells from hypoxia-mediated cell death by suppressing BNIP3 expression then preventing the openings of mPTP. In the heart, the openings of mPTP are likely involved in the mechanism of myocardial damage due to the reperfusion after ischemia. The prolonged opening of mPTP is considered one of the endpoints of the cascade to myocardial damage, causing loss of cardiomyocyte function and viability. Therefore, the blockage of mPTP openings by M4N is considered to be beneficial for preventing further damages of cardiomyocyte after reperfusion.

The inventors' data on mitochondrial metabolism and membrane potential in LNCAP cells indicates that M4N has an activity to suppress mitochondrial metabolism and to induce hyperpolarization of $\Delta\Psi_m$ (data not shown). It has been shown by many studies that the up-regulation of mitochondrial metabolism after recovery of oxygen supply is one of the major driving forces to initiate cell death after ischemia, since cell death mechanisms require ATP to complete their functions. This suggests that this ability of M4N to suppress mitochondrial metabolism is among the major reasons why M4N can reduce cell death in HL-1 cells after hypoxia treatment.

In numerous clinical trials of M4N as an anticancer drug, it has been shown to be a very nontoxic and safe drug, which indicates that the blockage of BNIP3 expression itself should not be harmful to humans. The fact that BNIP3 knockout mice have been found to live without apparent abnormality serves as another indication that ablation of BNIP3 expression does not interfere in normal biological functions to a significant extent.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for the treatment of Ischemia/Reperfusion (IR) injury in the cardiac myocytes of a subject comprising administering to the subject during and/or after the ischemic event, the compound of formula (I),

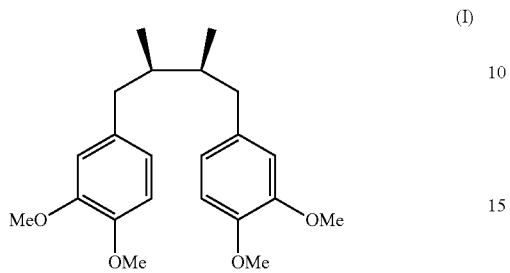

or a solvate, or stereoisomer thereof, in a sufficient amount to decrease the amount of IR injury.

2. The method of claim 1, wherein the amount administered to the subject is sufficient to provide a concentration in the blood of between 1 µM to 50 µM.

3. The method of claim 1, wherein the compound of formula (I), or a solvate, or stereoisomer thereof, is administered to the subject after reperfusion is initiated to the cardiac myocytes of the subject.

4. The method of claim 1, wherein the compound is administered to the subject with at least one additional therapeutic agent.

* * * * *